United States Patent [19]
Kynor et al.

[11] Patent Number: 5,603,321
[45] Date of Patent: Feb. 18, 1997

[54] ARTIFACT REMOVAL FROM PHYSIOLOGICAL SIGNALS

[75] Inventors: David B. Kynor; Christopher Haupt, both of San Diego; Steven Wilson, Del Mar, all of Calif.

[73] Assignee: Biomagnetic Technologies, Inc., San Diego, Calif.

[21] Appl. No.: 511,992

[22] Filed: Aug. 7, 1995

[51] Int. Cl.$^6$ .................................................. A61B 5/05
[52] U.S. Cl. .................... 128/653.1; 128/708; 128/901
[58] Field of Search ..................... 128/630, 653.1, 128/696, 704, 708, 901; 324/244, 248, 260

[56] References Cited

U.S. PATENT DOCUMENTS

| | | | |
|---|---|---|---|
| 4,793,361 | 12/1988 | DuFault | 128/696 |
| 5,318,036 | 6/1994 | Arand et al. | 128/901 |
| 5,365,934 | 11/1994 | Leon et al. | 128/708 |
| 5,372,139 | 12/1994 | Holls et al. | 128/708 |

OTHER PUBLICATIONS

Stephan Achenbach et al., "Elimination of Electronic Offset and Physiological Background Activity in Magnetocardiographic Localization," *Biomedizinische Technik*, Band 35 Erganzungsband (1990) pp. 160–161.

Plumb et al "A Noise Suppressor for Neurophysiological Recording of Impulse Activity", IEEE Transactions on Biomedical Engineering, vol. 11, No. 4, pp 157–159, 1964.

*Primary Examiner*—Ruth S. Smith
*Attorney, Agent, or Firm*—Gregory Garmong

[57] ABSTRACT

A measured magnetocardiography signal has a relatively small heart signal mixed with a large noise signal. To produce a heart signal having a reduced noise content, the times of occurrence of a time-series of isoelectric intervals of the measured signal is first determined and a time-series isoelectric artifact curve is formed from the measurements made at those times of occurrence. A time-series nonisoelectric artifact curve for other times is determined from this information. The time-series isoelectric and nonisoelectric artifact curve is subtracted from the measured magnetocardiography time-series signal to yield a time-series heart amplitude signal having reduced noise and undistorted form.

12 Claims, 3 Drawing Sheets

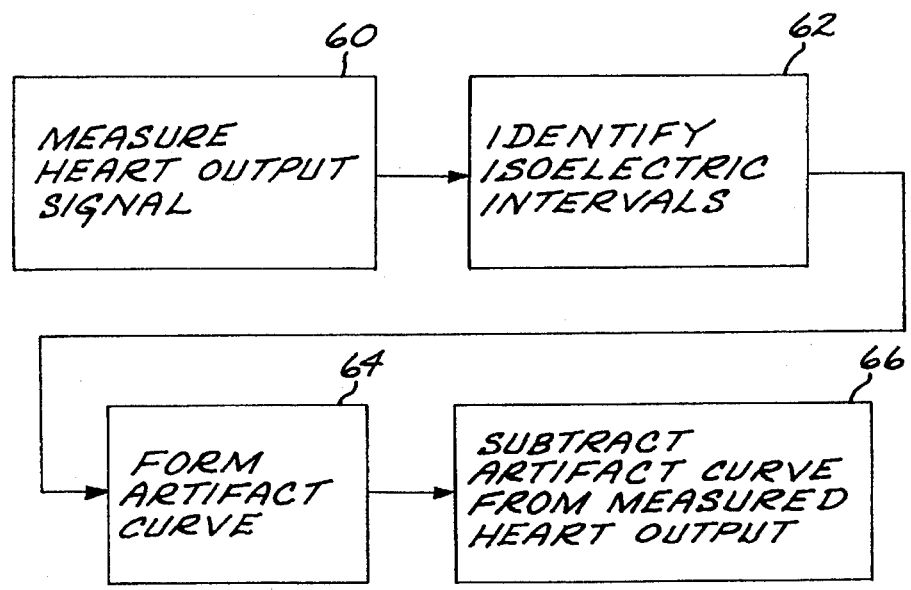
FIG.2
FIG.3
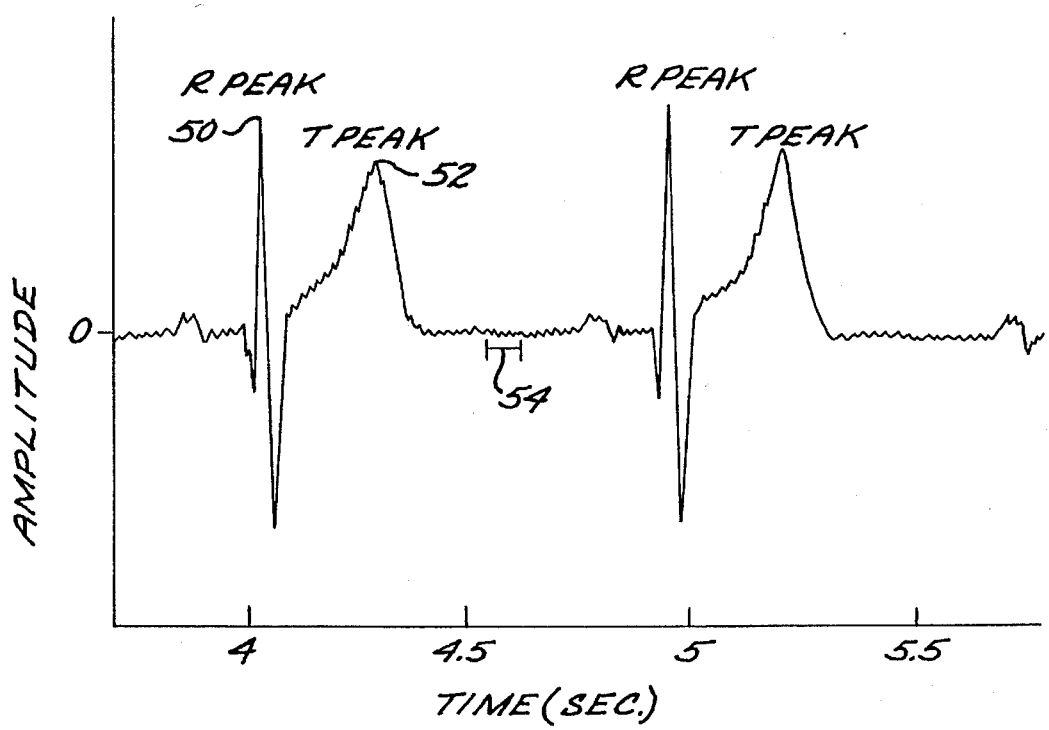

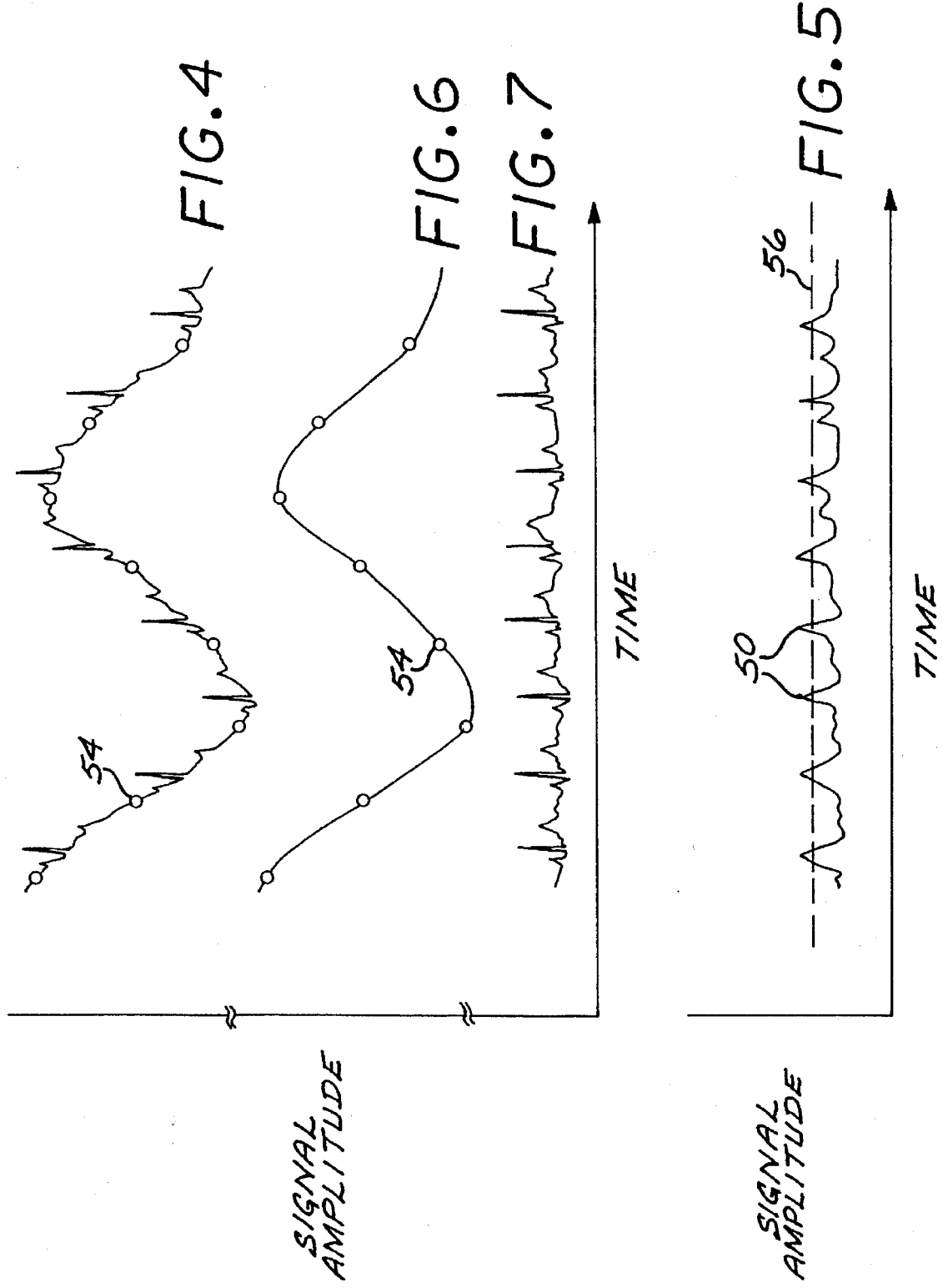

ARTIFACT REMOVAL FROM PHYSIOLOGICAL SIGNALS

BACKGROUND OF THE INVENTION

This invention relates to the measurement of physiological signals, and, more particularly, to obtaining a time-series heart signal by magnetocardiography.

The heart is a muscle that operates in response to a variety of electrical signals originating both inside and outside the heart. The electrical signals may be monitored and displayed, producing a time-series of heart signals. These cardiac cycle signals can, in turn, be used to assess the health of the heart and the presence of some types of heart problems. The understanding of the functioning of the heart in health and in sickness may lie, in part, in determining the temporal and spatial relationships of various: sources of the measured electrical signals to each other.

Most studies of the heart and its electrical signals have been performed by electrocardiography (ECG). Electrical pickup sensors are attached to the surface of the body. The electrical signals produced during the functioning of the heart are detected and recorded, and are available for more detailed studies at a later time. The ECG signals show characteristic waveform shapes and patterns which physicians use to identify normal and abnormal heart function. In particular, there are regular intervals in the ECG signal pattern during which the ECG signal pattern is nearly zero, known as isoelectric intervals.

Magnetocardiography (MCG) provides an approach for detecting both the time series signal output and the locations of the sources of the electrical cardiac signals. This technique is based upon the fact that a magnetic field is generated by the electrical currents flowing in the heart. The magnetic field is detected by a sensitive magnetic field sensor, preferably an array of such sensors provided in a biomagnetometer, which is placed outside the body of a subject. The output of the sensors is amplified and filtered and made available for analysis.

In addition to the magnetic fields produced by the heart, the magnetic field sensors detect environmental magnetic fields which constitute noise that interferes with the measurement of the heart signals. Such environmental magnetic fields include the earth's magnetic field, magnetic fields produced by nearby electrical apparatus, and magnetic fields produced by completely unrelated equipment. The magnetic field produced by the heart is quite small compared to these environmental magnetic fields, and the cardiac signal can therefore be lost in the noise of the environmental magnetic fields.

It is therefore necessary to separate the cardiac magnetic field from the environmental magnetic fields with which it is mixed. One approach is to place the subject in a magnetically shielded room (MSR) that reduces the magnitude of the environmental magnetic fields that reach the sensors. Such MSRs are expensive, and the need to use such MSRs limits the use of magnetocardiography to those locations which have them. A second approach is to detect the noise component, and then seek to remove it by filtering. Conventional high-pass and band-pass analog and digital filters have been utilized for this purpose in the past. These techniques, which produce a filtered signal, have the shortcoming that they produce an output cardiac signal that is distorted from its true time-series values as a result of the filtering methodology. That is, the filtering removes not only the interference, but also components of the cardiac signal that lie in the same range of frequencies. The filtered, but distorted, signal may be used for some purposes, but for other purposes the distortions render the signal of significantly less value. In addition, digital filtering, the preferred filtering approach, consumes a significant amount of computer time when there are a large number of sensors whose outputs are to be processed. The signal analysis may therefore not be possible in real time, a drawback for some applications.

There is therefore a need for an improved approach to the study of the heart in which a true, undistorted time-series heart signal can be measured by magnetocardiography. Although measurements of heart signals are presently of most interest, the same improved approach may find application in relation to other physiological measurements. The present invention provides a necessary advance in the art toward fulfilling this need, and further provides related advantages.

SUMMARY OF THE INVENTION

The present invention provides an apparatus and method for measuring a time-series physiological signal front which noise due to the most significant environmental magnetic fields has been removed, which is particularly useful for measurement of signals produced by the heart. There is little distortion to the physiological signal resulting from the utilization of the approach. The measurement can be conducted substantially in real time without excessive utilization of processing resources, so that large numbers of channels of sensor information can be analyzed and presented.

In accordance with the invention, an apparatus measures a time-series signal generated by the heart and produces a time-series heart signal having a reduced noise content. The apparatus comprises sensor means for measuring a time-series of measured heart output amplitude signals having a noise component mixed therewith, and processing means for receiving the time-series of measured heart output amplitude signals and for producing a time-series heart amplitude signal having a reduced noise content. The processing means includes identification means for identifying the times of occurrence of a time-series of corresponding isoelectric intervals in the time-series of measured heart output amplitude signals, artifact modelling means for forming a corresponding isoelectric time-series of artifact amplitudes at the times of occurrence of the corresponding isoelectric intervals and for forming a non-isoelectric series of artifact amplitudes from the isoelectric time-series of artifact amplitndes, and subtraction means for subtracting the corresponding time-series of artifact amplitudes from the time-series of measured heart output amplitude signals to yield a time-series heart signal having reduced noise content. The processing means is preferably implemented with a programmable processor configured to perform these computations. The invention is equally applicable to the measurement of other physiological signals having a feature comparable to the isoelectric interval of the heart.

The apparatus is preferably implemented with a biomagnetometer and a programmable computer. The biomagnetometer has a magnetic field sensor with a sensor output, and an analog signal processor having a filter and an amplifier, which receives the sensor output and produces a measured heart output signal. The computer operates with various programmed configurations to digitally process the measured heart output amplitude signal. A time-series of isoelectric intervals in the measured heart output amplitude signal is first identified, preferably by identifying a time-series of the R-peaks in the measured heart output amplitude signal and locating the isoelectric intervals at fixed positions between the succeeding locations of the R-peaks. These isoelectric intervals, where there is substantially no electrical signal output amplitude from the heart itself, are used to determine a corresponding time-series artifact amplitude curve for both the isoelectric intervals and the non-isoelectric regions. The artifact curve is subtracted from the measured heart output amplitude signal to yield the time-series heart amplitude signal, which has reduced noise.

Typically, there are a plurality of magnetic field sensors and outputs, termed channels. These channels are each processed separately by the apparatus and approach just discussed. The resulting set of time-series heart signals can be used in any appropriate manner, such as forming a three-dimensional map of the electrical output of the heart using array imaging techniques.

The approach of the invention is directed primarily toward removing low-frequency artifacts, such as those caused by distant moving metallic objects, which are mixed into the measured heart signal. It is observed experimentally that these low-frequency, high amplitude artifacts are the principal noise component that is difficult to remove by other techniques such as conventional analog or digital filtering. The time-series heart signal produced in this way is minimally, if at all, distorted by the manner of its derivation, an important advantage.

Other features and advantages of the present invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 2 is a block diagram of an approach for practicing the present invention;

FIG. 3 is an idealized time-series heart output signal;

FIG. 4 is a trace of a time-series of measured heart output signals;

FIG. 5 is a trace of a time-series of measured heart output signals after high-pass filtering;

FIG. 6 is a trace of an artifact model corresponding to the time-series of measured heart output :signals of FIG. 3; and FIG. 7 is a trace of a time-series heart signal having a reduced noise content.

DETAILED DESCRIPTION OF THE PREFERRED EMBODIMENT

Figure 1:
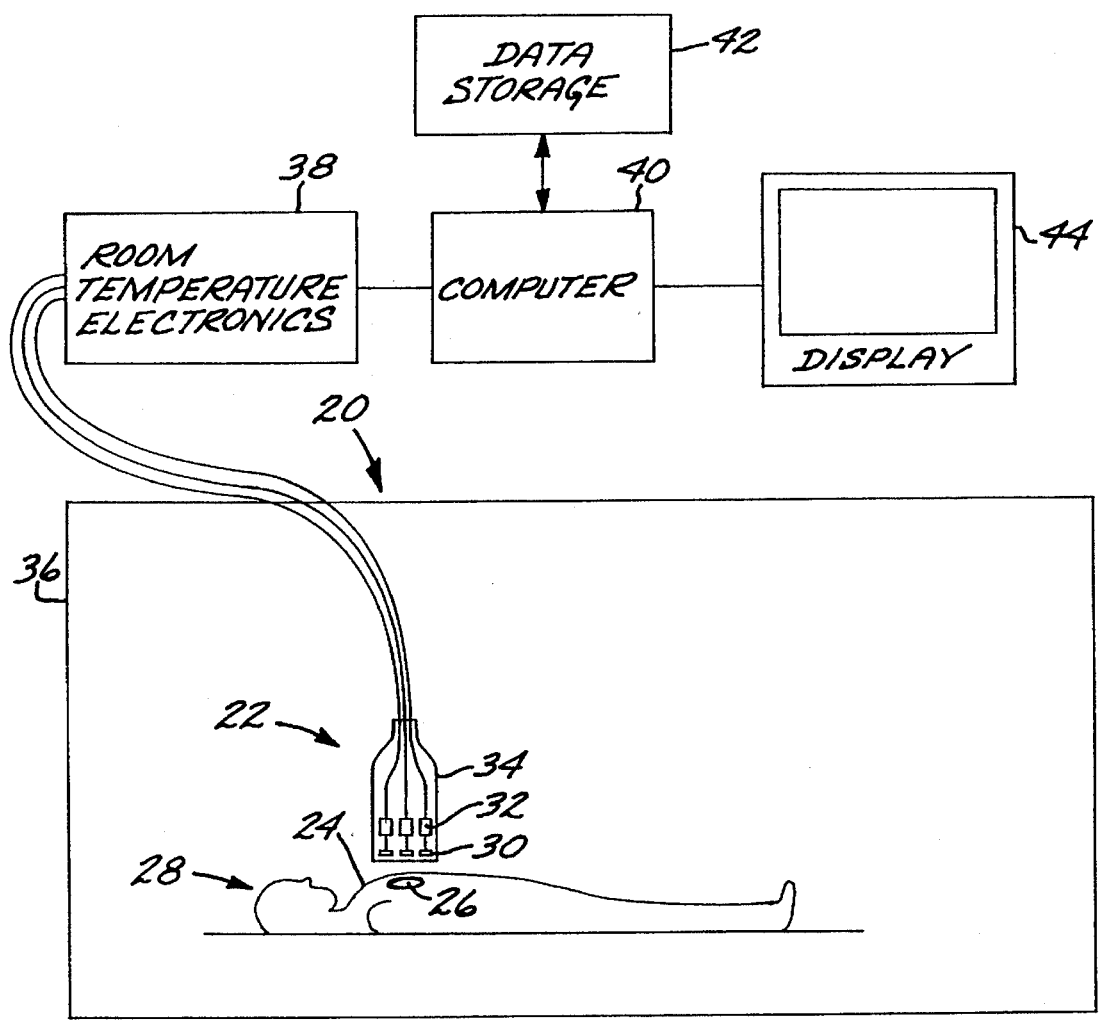
FIG. 1 is a schematic diagram of a biomagnetometer system.

FIG. 1 depicts a preferred apparatus 20 according to the present invention, and FIG. 2 illustrates the preferred method for practicing the invention. Referring to FIG. 1, the apparatus 20 utilizes a biomagnetometer 22 to detect magnetic fields produced by electric currents flowing within the body 24, and specifically within the heart 26, of a subject 28. The biomagnetometer 22 includes at least one, and preferably a plurality of, magnetic field pickup coils 30 that produce a small electric current responsive to a magnetic field flux. Each pickup coil 30 delivers its current to a sensitive magnetic field detector, preferably a superconducting quantum interference device ("SQUID") 32. The SQUID 32 and the pickup coil 30, which together comprise a sensor, are normally operated at a cryogenic temperature to attain maximum sensitivity. A cryogenic dewar 34 encloses the SQUID 32 and pickup coil 30 and provides such a cryogenic environment.

The subject 28, pickup coils 30, SQUIDs 32, and dewar 34 may optionally be located inside a magnetically shielded room 36 to minimize the effects of the environmental (external) magnetic fields that might otherwise be detected and erroneously thought to be produced by the heart. One result of the use of the present invention, however, is to reduce the need for using the magnetically shielded room 36 except in those cases that require the lowest-noise signal quality possible. The signals of the SQUIDs 32 are conducted to the exterior of the magnetically shielded room 36 to room-temperature electronics 38 that amplifies, conditions, and filters the signals. The resulting time-series of measured heart output signals is supplied to a computer 40 that performs signal processing. The computer may do real-time signal processing on the data, or store the information in a mass storage device 42 for later signal processing, or both. After the signals have been processed in the manner to be discussed in conjunction with FIG. 2, the results may be presented on a display 44.

Biomagnetometers and related structure are known in the art and are available commercially from companies such as Biomagnetic Technologies, Inc., San Diego, Calif. Biomagnetometers and their components are shown in U.S. Pat. Nos. 4,793,355; 4,773,952; 5,061,680; and 5,158,932. The operation of SQUID systems and their electronics are shown in U.S. Pat. Nos. 3,980,076; 4,079,730; 4,386,361; and 4,403,189. A magnetically shielded room is shown in U.S. Pat. No, 3,557,777. The disclosures of all of these patents are incorporated by reference.

This depicted approach is preferred, but other, less sensitive magnetic field detection approaches may be used, if desired. The detection of the magnetic field of the heart does not require as much sensitivity as does the detection of magnetic fields of the brain.

A preferred method according to the invention is illustrated in FIG. 2. The time-series heart output signal is measured, numeral 60. When the preferred apparatus of FIG. 1 is used, the measured heart output signal is the signal output by the room temperature electronics 38.

FIG. 3 schematically depicts two beats of the actual heart output signal, for reference. For the present purposes, the heart output signal can be characterized as having an R-peak 50, a T-peak 52, and an isoelectric interval 54 where there is a substantially zero signal amplitude.

FIG. 4 shows a typical time-series measured heart output signal, the output of the electronics 38 of FIG. 1. The component of the signal indicative of the heart output signal is mixed with a large amplitude, low-frequency noise component which is usually due to the presence of nearby machinery which produces a magnetic field. The heart signal of interest is thus of a small magnitude relative to the larger noise or artifact signal (although this relation is not a requirement for the operability of the invention).

The form of the artifact signal is determined by first identifying the corresponding isoelectric intervals 54 in the measured heart output signal of FIG. 4, numeral 62 (of FIG. 2), by any operable approach. In the preferred technique, the time locations of the R-peaks 50 are found and used to locate the isoelectric intervals. The R-peaks are located by configuring the computer 40 to high-pass filter the measured heart signal of FIG. 4 and rectify the high-pass component, producing a wave form such as shown in FIG. 5. In the preferred approach, the high-pass filtering is accomplished by bidirectional Butterworth digital filtering, a well-known technique described in A. Oppenheim and R. Schafer, "Digital Signal Processing," Prentice-Hall, Englewood Cliffs, N.J., 1975. The rectification is accomplished by taking the absolute value of each amplitude produced by the high-pass filtering. In the past, it has been known to perform a high-pass filtering of the measured heart output signal in order to achieve the final result. This approach results in some wave form distortion of the heart signal. In the present technique, the high-pass filtering is only a step of the procedure to obtain the temporal locations of the R-peak values, whose temporal locations are not shifted by the high-pass filtering. After the high-pass component is rectified, the highest peak, which is the R-peak 50, is detected. The detection of the R-peaks 50 is conveniently accomplished by finding the maximum values of the points that lie above a constant discrimination level 56 and that satisfy the timing relationship determined by the heart rate.

After the time-series of R-peaks 50 is determined, the isoelectric intervals 54 are located with reference to the R-peaks. From past observation, it is known that, in most instances, the isoelectric interval 54 is found in a fixed fractional range of the time between the R-peaks 50. In the preferred approach of the invention, the isoelectric interval 54 is selected to be a 5 millisecond period centered at a time location at about 55 percent of the time from a first R-peak to the next R-peak. This fraction can vary over a small range, as can be seen in FIG. 3. However, the preferred 55 percent is chosen to give a comfortable margin of error.

Thus, for example, in the preferred approach if a first R-peak is at 4 seconds and a second R-peak is at 5 seconds (60 heartbeats per minute), the isoelectric interval 54 is determined to be a 5 millisecond period centered at 4.55 seconds.

The isoelectric interval can be located by any other operable technique. For example, the isoelectric interval could be located relative to the T-peak that precedes the start of the isoelectric interval (rather than the R-peak, which follows the isoelectric interval), or any other feature of the heartbeat signal.

A corresponding artifact curve as shown in FIG. 6 is formed, numeral 64. The artifact curve is developed from the time-series of corresponding isoelectric intervals 54, by calculating the average value of the measured signal (the true heart signal mixed with the artifact signal as shown in FIG. 4) over each isoelectric interval determined in step 62 and plotting that average value at the time point about which the isoelectric interval is centered. At these isoelectric interval locations of the measured heart signal curve of FIG. 4, all of the signal amplitude is thus assumed to be due to the noise or artifact signal, a good assumption. A curve is then fitted through the plotted average values, as seen in FIG. 6, defining the non-isoelectric time-series of artifact values. The curve is preferably fitted through the plotted points using a four-point fit about each central value with a third-power polynomial. Such curve-fitting techniques are well established in the art, see, for example, P. Stark, "Introduction to Numerical Methods," Macmillan Publishing, New York, 1970.

The curve of FIG. 6 is an estimate of the artifact or noise portion of the measured magnetocardiographic signal of FIG. 4, for both the isoelectric interval and the non-isoelectric regions. To obtain a noise-corrected or true time-series heart signal, the time-series artifact curve of FIG. 6 is subtracted on a point-by-point basis from the time-series measured heart output signal of FIG. 4, numeral 66. The resulting time-series heart signal is depicted schematically in FIG. 7.

The step 60 is typically performed on a plurality of channels of the biomagnetometer. The steps 62, 64, and 66 are performed for the data of each channel, leading to a time-series heart signal as in FIG. 7 for each of the channels.

These steps are preferably accomplished using the computer 40 configured to perform the above-described operations in steps 62, 64, and 66. Such processing is rapid, as it involves only simple arithmetic operations. By contrast, most digital filtering techniques require Fourier analyzing the signal or the use of other complex, time-consuming procedures. Because the present approach provides for fast processing to obtain the time-series heart signal of FIG. 6, it permits multiple sensor channels to be processed in near-real time using currently available microcomputer technology. This capability provides near-real time information for the physician or researcher who is studying the heart, or for further processing such as array imaging of the source of the electrical signal. Such array imaging is disclosed, for example., in U.S. Pat. Nos. 4,977,896 and 5,269,325, whose disclosures are incorporated by reference. Alternatively, the data can be stored in the data storage device 42 for later processing or re-processing.

The invention is preferably applied for the analysis of cardiac signals, as just described. Other physiological applications can also be made, wherein there is a period that corresponds to the isoelectric signal for heartbeats. Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. Apparatus for measuring a time-series signal generated by the heart and producing a time-series heart signal having a reduced noise content, the apparatus comprising:

sensor means for measuring a time-series of measured heart output amplitude signals having a noise component mixed therewith; and processing means for receiving the time-series of measured heart output amplitude signals and for producing a time-series heart amplitude signal having a reduced noise content, the processing means including identification means for identifying the times of occurrence of a time-series of corresponding; isoelectric intervals in the time-series of measured heart output amplitude signals, artifact modelling means for forming a corresponding isoelectric time-series of artifact amplitudes at the times of occurrence of the corresponding isoelectric intervals and for forming a non-isoelectric series of artifact amplitudes from the isoelectric time-series of artifact amplitudes, the isoelectric and the non-isoelectric series together comprising the time-series of artifact amplitudes; and subtraction means for subtracting the time-series of artifact amplitudes from the time-series of measured heart output amplitude signals to yield a time-series heart signal having reduced noise content.

2. The apparatus of claim 1, wherein the sensor means comprises a biomagnetometer including a magnetic field sensor having a sensor output, and a room temperature electronics unit which receives the sensor output, the room temperature electronics unit including a filter and an amplifier.

3. The apparatus of claim 1, wherein the processing means comprises a programmable computer.

4. The apparatus of claim 1, wherein the identification means comprises a programmable computer configured to identify an R-peak of the measured heart output signal and to determine the isoelectric interval relative to the R-peak.

5. The apparatus of claim 1, wherein the identification means comprises means for high-pass filtering the measured heart output amplitude signal to form a filtered heart output signal;

means for detecting portions of the filtered heart output signal having an amplitude greater than a preselected amplitude value as a time series of R-peaks; and means for selecting an isoelectric interval at a preselected time fraction of the interval between succeeding R-peaks of the time series of R-peaks.

6. The apparatus of claim 1, wherein the artifact modelling means comprises a programmable computer configured to fit a polynomial function to a time-series.

7. The apparatus of claim 1, wherein the subtraction means comprises a programmable computer configured to subtract the corresponding time-series of artifact amplitudes from the time-series of measured heart output amplitude signals.

8. The apparatus of claim 1, wherein the sensor means comprises a plurality of magnetic field sensor channels, each sensor channel having a sensor channel output, and wherein the processing means comprises multichannel processing means for receiving each sensor channel output and producing a corrected heart signal having a reduced noise content for each sensor channel output, on a channel-by-channel basis.

9. Apparatus for measuring a time-series signal generated by a living subject and producing a time-series physiological signal having a reduced noise content, the apparatus comprising:

a biomagnetometer including
  a magnetic field sensor having a sensor output, and
  an electronics unit which receives the sensor output and produces a measured physiological output signal, the electronics unit including a filter and an amplifier; and a computer configured to first identify the times of occurrence of a time-series of corresponding isoelectric intervals in the time-series of measured physiological output amplitude signals, second form a time-series of corresponding isoelectric artifact amplitudes at the times of occurrence of the isoelectric intervals, third form a time-series of non-isoelectric artifact amplitudes from the isoelectric time-series of artifact amplitudes, and fourth subtract the time-series of isoelectric and non-isoelectric artifact amplitudes from the time-series of measured physiological output amplitude signals to yield a time-series physiological signal having reduced noise content.

10. A method for obtaining a time-series heart signal, comprising the steps of measuring a time-series of measured heart output amplitude signals having a noise component mixed therewith; and receiving the time-series of measured heart output amplitude signals and producing a time-series heart amplitude signal having a reduced noise content, the step of receiving including the steps of identify the times of occurrence of a time-series of corresponding isoelectric intervals in the time-series of measured heart output amplitude signals, forming a corresponding time-series of isoelectric artifact amplitudes at the times of occurrence of the corresponding isoelectric intervals and a time-series of non-isoelectric artifact amplitudes at other times, and subtracting the corresponding time-series of isoelectric and non-isoelectric artifact amplitudes from the time-series of measured heart output amplitude signals to yield a time-series heart signal having reduced noise content.

11. The method of claim 10, wherein the step of measuring includes the step of providing a biomagnetometer including
  a magnetic field sensor having a sensor output, and
  an electronics unit which receives the sensor output, the electronics unit including a filter and an amplifier.

12. The method of claim 10, wherein the step of receiving includes the step of providing a programmable computer.

* * * * *